United States Patent [19]

Dietrich et al.

[11] Patent Number: 4,757,097
[45] Date of Patent: Jul. 12, 1988

[54] PROCESS FOR THE PRODUCTION OF OLIGOESTERS CONTAINING HYDROXY GROUPS AND THEIR USE

[75] Inventors: Manfred Dietrich, Leverkusen; Manfred Kapps, Bergisch Gladbach; Klaus König, Odenthal; Roland Nast, Dormagen, all of Fed. Rep. of Germany

[73] Assignee: Bayer Aktiengesellschaft, Bayerwerk, Fed. Rep. of Germany

[21] Appl. No.: 65,486

[22] Filed: Jun. 23, 1987

[30] Foreign Application Priority Data

Jun. 24, 1986 [DE] Fed. Rep. of Germany ....... 3621039

[51] Int. Cl.$^4$ .............................................. C08G 18/14
[52] U.S. Cl. ..................................... 521/167; 521/172; 521/173; 528/76; 528/77; 528/78; 528/79; 528/291; 560/88; 560/91
[58] Field of Search ...................... 521/167, 172, 173; 528/76, 77, 78, 79, 291; 560/88, 91

[56] References Cited

U.S. PATENT DOCUMENTS

| 2,779,783 | 1/1957 | Hayes | 260/485 |
| 2,863,855 | 12/1958 | Wilson et al. | 260/75 |
| 2,932,622 | 4/1960 | Bioch | 260/4 |
| 3,374,208 | 10/1962 | Seiner et al. | 260/78.4 |
| 3,414,608 | 12/1968 | Fujita et al. | 260/475 |
| 3,455,886 | 7/1969 | Versnel | 260/78.4 |
| 3,459,733 | 8/1969 | Byrd et al. | 210/24 |
| 3,459,788 | 8/1969 | Enoki et al. | 260/472 |
| 4,452,997 | 6/1984 | Marx et al. | 560/200 |
| 4,582,926 | 4/1986 | Strachle et al. | 560/91 |

FOREIGN PATENT DOCUMENTS

| 715201 | 9/1968 | Belgium . |
| 1248660 | 8/1967 | Fed. Rep. of Germany . |
| 1568883 | 8/1970 | Fed. Rep. of Germany . |
| 623669 | 5/1949 | United Kingdom . |
| 1060750 | 3/1967 | United Kingdom . |
| 1145765 | 3/1969 | United Kingdom . |

OTHER PUBLICATIONS

Methoden der Organischen Chemie, vol. VIII, 1952, pp. 531–533, Houben–Weyl, Georg Thieme Verlag.

Primary Examiner—Maurice J. Welsh
Attorney, Agent, or Firm—Gene Harsh; Joseph C. Gil; Lyndanne M. Whalen

[57] ABSTRACT

Oligoesters having hydroxyl groups and an OH number of from 200 to 600 mg KOH/g are made by reacting a cyclic dicarboxylic acid anhydride in which no halogen is present with a polyfunctional alcohol or dialkanolamine in a molar ratio of from 1:0.5 to 1:1.5 at a temperature of from 50° to 150° C. to form the corresponding dicarboxylic acid semiester and/or semiamide. This semiester and/or semiamide is then alkoxylated with ethylene oxide and/or propylene oxide in the presence of a catalyst at 80° to 150° C. The equivalent ratio of acid groups to alkylene oxide groups is from 1:0.8 to 1:1.7. The catalysts are reaction products of alkoxides with at least 3 C-atoms with ammonia, piperidine, piperazine and/or $C_2$–$C_6$ aliphatic, polyamines, preferably diamines in which all of the NH-functional groups have been alkoxylated. The resultant oligoester may then be reacted with a polyisocyanate optionally in the presence of known additives, such as blowing agents and catalysts.

14 Claims, 4 Drawing Sheets

4,757,097

PROCESS FOR THE PRODUCTION OF OLIGOESTERS CONTAINING HYDROXY GROUPS AND THEIR USE

BACKGROUND OF THE INVENTION

This invention relates to a process for the production of hydroxy-group-containing oligoesters during which no halogen is present. These oligoesters have a particularly favorable molecular weight distribution and are useful in the production of flame resistant polyisocyanate addition products.

In the field of rigid polyurethane foams, improved flame-resistance has acquired increasing significance, particularly where the foams are used in the construction industry. In view of more stringent legal requirements concerning burning behavior, it has also been necessary in recent years to intensify the search for starting materials from which it is possible to produce rigid polyurethane foams which are capable of complying with the stricter legal standards. In most attempts to satisfy these requirements, the proportion of flame-proofing agent used in polyether-based foam formulations has had to be greatly increased. However, exclusive use of inexpensive, non-functional flameproofing agents, such as tris-$\beta$-chloroethylphosphate, tris-$\beta$-chloroisopropylphosphate or diphenylcresylphosphate, requires such large amounts of these materials that the foams obtained are unusable. It was therefore necessary to add halogenated and/or phosphorus-containing polyols to such formulations. Unfortunately such polyols add greatly to the cost of the formulations.

However, if the long-established polyether polyols, for example sugar-, glycerol- or sorbitol-started polyalkylene oxides having OH numbers of from 300 to 550, are replaced by polyester-based polyols having OH numbers in the same range, much smaller quantities of additional flame-retarding agents can be used to satisfy the relevant flame-proofing standards. There would therefore, be no need to use the expensive functional flame-retarding agents because the inexpensive, non-functional types would be sufficient.

Polyesters having OH numbers of from 300 to 550 produced by condensation of dicarboxylic acids with diols have a relatively high viscosity as a result of the natural broad oligomer distribution (Flory distribution) which makes them difficult to process. In addition, the content of unesterified free diol is extremely high. For example, a polyester of phthalic acid anhydride and diethylene glycol having an OH number of 300 contains approx. 13 wt. % free diethylene glycol. This leads to processing difficulties due to both viscosity and incompatibilities with the polyisocyanates and fluorinated hydrocarbon blowing agents used.

The above-mentioned disadvantages of viscosity and incompatibility occur to a greater extent in cases where, in addition to the diols, alcohols of relatively high functionality are used to produce the polyesters. Functionalities above 2 are desirable and sometimes necessary to obtain good foaming properties (hardening, dimensional stability, etc.). For these reasons, there has been no shortage of attempts to produce polyesters from dicarboxylic acids or dicarboxylic acid semiesters by alkoxylation reactions, i.e. reaction with alkylene oxides. Such an alkoxylation process would be advantageous because there would be a greater chance of obtaining products of narrow molecular weight distribution having a lower viscosity than corresponding polycondensates and containing very little, if any, free alcohol component. Economic considerations also support this approach because commercially inexpensive materials would be used.

The processes described in the literature do not however meet the above-mentioned expectations because either esterifications or transesterifications occur under the conditions applied, so that products of broad molecular weight distribution are ultimately formed. Alkoxylation of the OH groups present also occurs to a large degree in addition to the desired esterification. Consequently, polyether esters having a distinctly reduced flame retarding effect in rigid polyurethane foams are formed as the end products. In most cases, both the esterification and alkoxylation secondary reactions occur at one and the same time. In some cases, a very large excess of alkylene oxides has to be used to achieve a high conversion of the carboxyl groups and has to be removed by distillation on completion of the reaction. However, a procedure such as this is attended by serious disadvantages and dangers when used for production on an industrial scale.

According to U.S. Pat. Nos. 3,455,886 and 3,459,733, from 2 to 8 moles alkylene oxide per mole dicarboxylic acid semiester are required in the absence of catalysts to achieve acid numbers below 1 mg KOH/g. It was soon recognized that special catalysis is necessary for a more selective reaction. According to U.S. Pat. No. 2,779,783 or DE-A 1,568,883, alkoxylation in the presence of alkali metal halides, carbonates or hydroxides results in more selective reaction. However, alkali metal halides lead to corrosion problems and, in addition, have to be filtered off. Alkali metal carbonates or hydroxides remain as carboxylates in the polyester, unless they are neutralized and filtered, and affect the reactivity of corresponding polyurethane formulations. In addition, our own tests have shown that, under the necessary reaction conditions, transesterifications take place to a large degree, leading to increased viscosities and end products which are scarcely different from the polyesters produced by condensation (cf. Comparison Example 2a) in accordance with the prior art. In addition to transesterifications, alkali metal carbonates or hydroxides lead to a large degree to undesirable ether formation through alkoxylation of the OH groups. Large excesses of alkylene oxide are therefore necessary to obtain low acid numbers.

DE-A No. 1,248,660 and DE-A No. 3,201,203 describe the reaction of dicarboxylic acids or semiesters thereof with alkylene oxides in the presence of thiodialkylene glycols, such as thiodiglycol or thiodipropylene glycol. Although the reaction is largely unaccompanied by secondary reactions, the use of these catalysts leads to serious odor problems both during the production and during the further processing of these products. Such odors are not tolerated by the foam manufacturers. The production of polyesters by reaction of carboxylic acid anhydrides with alkylene oxides in the absence of water and in the presence of glycols and catalysts is described in U.S. Pat. No. 3,374,208. The catalysts disclosed are metal compounds with a zinc, tin, manganese, lead, nickel, cobalt or cadmium cation and an oxygen, chlorine, acetate, butyrate, phosphate, nitrate, stearate, oleate or naphthenate anion.

It is also known that carboxylic acids can be esterified with alkylene oxides in the presence of catalysts such as sulfuric acid, sodium acetate, iron(III) chloride, etc. (see Methoden der Organischen Chemie, Vol. VIII, Houben-Weyl, Georg Thieme Verlag, Stuttgart, 1952, pages 531-533). Chromium(III) compounds (e.g. chromium octoate) are used for the alkoxylation of aromatic carboxylic acids in the processes disclosed in NL-A No. 67-01261 and in BE-B No. 715 201. However, use of the chromium and other salts results in discoloration of the product which is extremely difficult to remove and requires undesirably high quantities of ethylene oxide to obtain low acid numbers. Many disclosures (FR-A No. 1,428,204, GB-B No. 623,669, GB-B No. 1,060,750, U.S. Pat. No. 2,932,622, U.S. Pat. No. 2,863,855, U.S. Pat. No. 3,414,608, DE-A No. 3,315,381) describe the use of tertiary amines such as trialkylamines, pyridine, imidazole, N-methylimidazole, phosphines or triethanolamine as catalysts. Unfortunately these amines all give rise to one or more of the disadvantages mentioned above. In addition, some amines can cause serious discoloration of the products, presumably due to quaternization of the tertiary nitrogen, so that unacceptable products are obtained. Aromatic nitrogen compounds, such as N-methylimidazole (see Comparison Example 2b infra) are outstanding transesterification catalysts and, accordingly, give products having an undesirably broad molecular weight distribution.

SUMMARY OF THE INVENTION

It is an object of the present invention to provide oligoesters having an OH number of from 200 to 600 mg KOH/g and a process for their production in which no halogen is present in the reaction mixture.

It is also an object of the present invention to provide a process for producing oligoesters which does not result in discoloration of the oligoester and which produces oligoesters having a relatively narrow molecular weight distribution.

It is a further object of the present invention to provide oligoesters which are useful in the production of polyisocyanate-based plastics, particularly flame resistant foams.

These and other objects which will be apparent to those skilled in the art are accomplished by reacting a cyclic dicarboxylic acid anhydride in which no halogen is present with a polyfunctional alcohol or dialkanolamine in a molar ratio of from 1:0.5 to 1:1.5 at a temperature of from 50° to 150° C. to form the corresponding dicarboxylic acid semiester and/or semiamide. This semiester and/or semiamide is then alkoxylated with ethylene oxide and/or propylene oxide in the presence of a catalyst 80° to 150° C. The equivalent ratio of acid groups to alkylene oxide groups is from 1:0.8 to 1:1.7. The catalyst are reaction products of alkoxides with at least three C-atoms with ammonia, piperidine, piperazine and/or $C_2-C_6$ aliphatic, polyamines, preferably diamines in which all of ths NH-functional groups have been alkoxylated. The resultant oligoester may then be reacted with a polyisocyanate optionally in the presence of known additives such as blowing agents and catalysts.

DETAILED DESCRIPTION OF THE INVENTION

Figure 1:
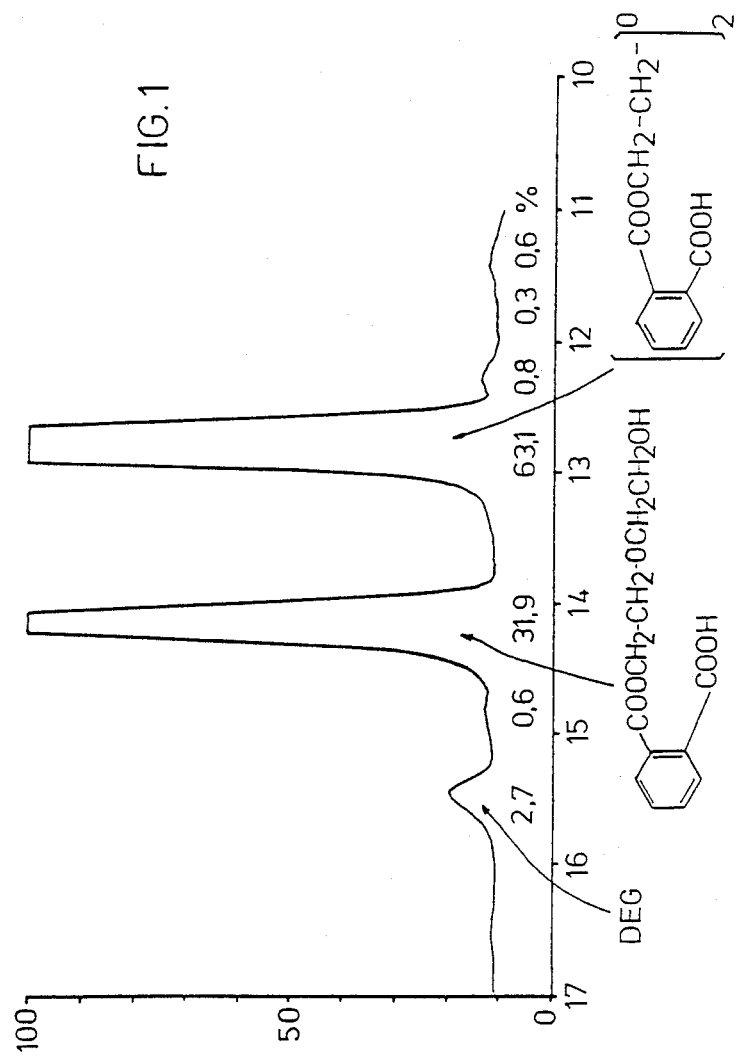
FIGS. 1 and 2 are gel chromatograms for the product of Example 2.

It has now surprisingly been found that oligoesters can be obtained by reacting dicarboxylic acid semiesters with alkylene oxides without any of the disadvantages of the prior art processes by using special reaction products of alkoxides with e.g. ammonia, ethylene, propylene or hexamethylenediamine as catalysts. These catalysts allow the starting products containing carboxyl groups to be reacted with the alkylene oxides under mold conditions because only small excesses of alkylene oxide are required for complete or substantially complete reaction. In addition, clear to faintly colored products are obtained which do not require any aftertreatment, such as neutralization or filtration. The catalysts may safely remain in the product because, in the applications in question, products of the same type or similar products are in any case often present in the formulations. In products containing tertiary amino groups, the nitrogen appears to be sterically hindered in such a way that, although it still sufficiently catalyzes the reaction of carboxyl groups with alkylene oxides, it is no longer suitable for quaternization reactions or as a catalyst for esterifications, transesterifications or alkoxylations of the OH-groups.

Accordingly, the present invention is directed to a process for the production of oligoesters containing hydroxyl groups having an OH number of from 200 to 600 mg KOH/g which does not employ any halogen-containing reactant by reacting of dicarboxylic acid anhydrides with polyfunctional alcohols and/or dialkanolamines in a molar ratio of 1:0.5 to 1.5 (preferably in a molar ratio of 1:07 to 1.2) to form the corresponding dicarboxylic acid semiesters and/or semiaides at temperatures of from 50° to 150° C. preferably at temperatures of from 90° to 130° C.) and subsequent alkoxylation with ethylene oxide and/or propylene oxide using an equivalent ratio of acid groups to alkylene oxides of 1:0.8 to 1.7 at temperatures of from 80° to 150° C. (preferably at temperatures of from 90° to 130° C.). This process is characterized by the presence of reaction products of alkoxides with at least three C-atoms with ammonia, piperidine, piperazine and/or $C_2-C_6$ aliphatic polyamines, preferably of ammonia, ethylene, propylene or hexamethylenediamine, in which all of the NH functions are alkoxylated as catalyst for the acid/alkylene oxide reaction. The present invention is also directed to a process for the production of polyurethane plastics, preferably PU foams, including polyisocyanurate foams, which in particular show flame resistant properties from the oligoesters of the present invention. The inventive oligoesters may be used with other polyester of polyether polyols and incorporable or non-incorporable flameproofing agents known to be useful in polyisocyanate polyaddition processes.

The starting materials useful in the production of the oligoesters of the present invention include: cyclic, aliphatic and aromatic dicarboxylic acid anhydrides such as maleic acid anhydride, itaconic acid anhydride, citraconic acid anhydride, succinic acid anhydride, glutaric acid anhydride, phthalic acid anhydride and tetrahydrophthalic acid anhydride. Maleic acid anhydride and/or phthalic acid anhydride and/or glutaric acid anhydride are preferably used.

Polyhydric alcohols useful for the ring-opening esterification with the anhydrides include: diols such as ethylene glycol, 1,3- and 1,2-propane diol, diethylene glycol, dipropylene glycol, tripropylene glycol, 1,3-pentane diol, 1,6-hexane diol, 1,4-3,6-dianhydrohexitols; and higher alcohols, such as glycerol, trimethylol ethane, trimethylol propane, 1,2,6-hexane triol, α-methylglycoside, pentaerythritol and sorbitol. Ethylene glycol, diethylene glycol, propylene glycol, trimethylol propane, glycerol and sorbitol are preferred. The polyhydric alcohols having functionalities of >may be used either on their own or in admixture with diols.

Alkanolamines which may be used either on their own or in admixture with polyhydric alcohols for the ring-opening esterification with the anhydrides include: N-methyl, N-ethyl and N-butyl ethanolamine and dialkanolamines such as diethanolamine, dipropanolamine and dibutanolamine.

The catalysts used for alkoxylation of the carboxyl groups are reaction products of alkoxides with at least 3 C-atoms with amines specifically propoxylation products of ammonia or lower aliphalic or cyclic aliphatic diamines, particularly those containing from 2 to 6 C-atoms, in which all of the NH-functions are completely propoxylated, preferably (completely) propoxylated products of ammonia and propoxylated ethylenediamine, 1,2-propylenediamine and 1-hexamethylenediamine containing from 4 to 12 (preferably from 5 to 7) moles propylene oxide per mole diamine.

Instead of propoxylation products reaction products of butylene oxide, styrene oxide may be used.

Suitable for catalysts, triisopropanolamine, tetraisopropanoethylenediamine, -propylenediamine, -butylenediamine, -hexamethylenediamine, -methylpetanediamine and -dimethylbutanediamine, further higher homologues of ethylene diamine such as diethylene triamine, triethylene tetramine, tetraethylene pentamine or higher homologues of propylene diamine such as dipropylene diamine. It is also possible, although less preferred, to use 2-hydroxylpropyl piperidine or, better still, bis-(2-hydroxypropyl)-piperazine or bis-(2-hydroxypropyl)-2,5-dimethylpiperazine.

Ethylene oxide or propylene oxide of mixtures of these two epoxides are used as the alkylene oxides for alkoxylation of the carboxyl groups.

To produce the oligoesters of the present invention, the dicarboxylic acid semiester and/or the dicarboxylic acid semiamide is initially prepared from the polyfunctional alcohol and/or dialkanolamine and a cyclic dicarboxylic acid anhydride at temperatures of from 50° to 150° C. preferably from 90° to 130° C. over a reaction time of from 1 to 10 hours, preferably from 2 to 4 hours. The cyclic dicarboxylic acid anhydrides are reacted with the polyfunctional alcohols and/or dialkanolamides in a molar ratio of 1.0.5 to 1.5, preferably 1:0.7 to 1.2. The dicarboxylic acid semiesters and/or semiamides obtained are then reacted with ethylene oxide and/or propylene oxide in the presence of from 0.5 to 5 parts by weight of one of the catalysts according to the invention at a temperature of from 80° to 150° C., preferably from 90° to 130° C. using an equivalent ratio of acid groups to alkylene oxide of 1:0.8 to 1.7, preferably of 1:1.0 to 1.6. Acid numbers below 10 are the goal. The quantity of alkylene oxide used is selected so that very little, if any, free alkylene oxide is present after application of the described reaction conditions. Any traces of free alkylene oxides still present are distilled off under reduced pressure. Some of the cyclic dicarboxylic acid anhydrides used show a tendency towards sublimation at the temperature required for ring opening. Accordingly, the required alkoxylation catalysts of the present invention are preferably used during the actual ring-opening step because they provide for more rapid semiester formation at low temperatures.

The end products of the process are more or less viscous, light liquids, depending upon the formulation. It is possible to obtain acid numbers below 1 under mild conditions and with a small excess of ethylene oxide by the process of the present invention. However, acid numbers of up to 10 are acceptable where the products are used as a polyol component in polyurethane and/or polyisocyanurate foams. The products of the present invention are distinguished by low viscosities. Their low viscosities are attributable to the fact that the oligoesters are not in a statistical equilibrium, as in the case of the polycondensates, but instead show a narrow molecular weight distribution. Despite the catalysts present in them, the products of the invention surprisingly show no tendency, after prolonged periods at temperatures of up to 130° C., towards equilibration with increased viscosity, as normally occurs where known prior art catalysts are used. The oligoesters of the present invention are eminently suitable as starting materials for polyurethane plastics where polyhydroxyl compounds having high OH numbers are normally used, for example in coatings, bonds, duromer, sandwich materials, etc. However, their principle field of application is in rigid polyurethane foams, preferably flame resistant rigid polyurethane foams having different polyisocyanurate contents.

In addition to the oligoesters and the catalysts of the present invention, the materials described more fully below are used for the production of polyurethanes, preferably rigid polyurethane foams.

Polyisocyanates useful in the production of polyurethanes in accordance with the present invention include: aliphatic, cycloaliphatic, araliphatic, heterocyclic and, in particular, aromatic di- and/or polyisocyanates of the type described, for example, by W. Siefken in Justus Liebigs Annalen der Chemie, 562, pages 75 to 136, for example those corresponding to the formula

Q(NCO)$_n$ in which
n=2 to 4, preferably 2, and Q represents an aliphatic hydrocarbon radical containing from 2 to 18 (preferably from 6 to 12) C-atoms, a cyclo- aliphatic hydrocarbon radical containing from 4 to 20 (preferably from 5 to 11) C-atoms, an aromatic hydrocarbon radical containing from 6 to 20 (preferably from 6 to 13) C-atoms or an araliphatic hydrocarbon radical containing from 8 to 15 (preferably from 8 to 13) C-atoms. Such polyisocyanates are described in DE-A No. 2,832,253, pages 10 to 11. It is particularly preferred to use the commercially readily obtainable polyisocyanates such as 2,4- and/or 2,6-tolylene diisocyanate and mixtures of these isomers ("TDI"); diphenylmethane diisocyanates (4,4'- and/or 2,4'- and/or 2,2'-isomers); polyphenyl-polymethylene polyisocyanates of the type obtained by phosgenating aniline- formaldehyde condensates ("crude MDI"); and "modified polyisocyanates", i.e. polyisocyanates containing carbodiimide groups, urethane groups, allophanate groups, isocyanurate groups, urea groups and/or biuret groups, particularly those modified polyisocyanates which are derived from 2,4- and/or 2,6-tolylene diisocyanate and preferably from 4,4'- and/or 2,4'-diphenylmethane diisocyanate. Where only difunctional compounds of relatively high molecular weight and, optionally, other only difunctional chain-extending agents of low molecular weight are used, it is preferred to use modified polyisocyanates having a functionality of more than 2.0 preferably trifunctional and/or higher polyisocyanates.

Other starting materials which may optionally be used in the production of polyurethanes include so-called chain extending agents or crosslinking agents, i.e. compounds containing at least 2 isocyanate-reactive hydrogen atoms and having a molecular weight of from 18 to 399. The chain extending or crosslinking agents are preferably compounds containing hydroxyl groups and/or amino groups and/or thiol groups and/or carboxyl groups and/or hydrazide groups, most preferably compounds containing hydroxyl groups and/or amino groups. These compounds generally contain from 2 to 8 and preferably from 2 to 4 isocyanate-reactive hydrogen atoms. Examples of these compounds can be found in DE-A No. 2,832,253, pages 19-20. Specific examples include: water, hydrazine, ethylene glycol, 1,4-butane diol, trimethylol propane, formitol mixtures and adipic acid dihydrazide.

Compounds containing at least two isocyanate-reactive hydrogen atoms and having a molecular weight of from about 400 to 10,000 may be used as a relatively high molecular weight co-polyol component in a quantity of up to approximately 80 wt. %, based on the oligoester polyol(s) of the present invention. Compounds containing amino groups, thio groups or carboxyl groups may be used but it is preferred that compounds containing hydroxyl groups, more especially compounds containing from 2 to 8 hydroxyl groups, particularly those having a molecular weight of from 600 to 6000 (preferably of from 1500 to 4000), most preferably polyesters, polyethers, polythioethers, polyacetals, polycarbonates and polyester amides containing from 2 to 4 hydroxyl groups of the type known to be useful for the production of homogeneous and cellular polyurethanes (described, for example, in DE-A No. 2,832,253, pages 11 to 18) be used. Particular preference is attributed to polyethers obtained by addition of one or more alkylene oxides (ethylene oxide and particularly propylene oxide) onto difunctional or polyfunctional "starters" (polypropylene glycol, glycerol, sorbitol, formose, sucrose, triethanolamine, trimethylol propane) and to polyethers containing dispersed or dissolved polyaddition products of diisocyanates and hydrazine and/or diamines and/or glycols or polymers and/or graft polymers (preferably of styrene and acrylonitrile). The preferred polyethers have an average functionality above 2.0.

Auxiliaries and additives, such as the readily volatile inorganic, preferably organic substances commonly used as blowing agents, known catalysts such as tertiary amines, tin(II) and tin(IV) compounds, surface-active additives, such as emulsifiers and foam stabilizers; reaction retarders, for example acid-reacting substances, such as hydrochloric acid or organic acid halides; known cell regulators such as paraffins, fatty alcohols and dimethylpolysiloxanes; known pigments and dyes; stabilizers against the effects of aging, light and weather; plasticizers; fungistatic and bacteriostatic agents and fillers, may optionally be added. These auxiliaries and additives which may optionally be used in accordance with the invention are described in detail, for example in DE-A No. 2,732,292, pages 21 to 24. Further examples of suitable auxiliaries and additives can be found on pages 103 to 113 of Kunststoff-Handbuch, Vol. VII, edited by Vieweg and Hochtlen, Carl-Hanser-Verlag, Munich 1966, and on pages 92 to 111 of Kunststoff-Handbuch, Vol. VII, edited by Becker and Braun, Carl-Hanser-Verlag, Munich 1983.

Rigid foams produced using the oligoesters of the present invention may be used as insulating boards, as sandwich elements with various surface layers, as in-situ foams, as injected foams, or foams produced by overcoating, as solar collector fillings, as tube insulations, as filling and assembly foams and as block foams.

Such foams may be produced by standard, continuous batch-type polyurethane processing techniques, such as for example the laminator technique, spraying or casting, using high-pressure or low-pressure foaming machines. Their relatively low viscosities of the oligoesters are particularly advantageous in machine processing.

The invention is further illustrated but is not intended to be limited by the following examples in which all parts and percentages are by weight unless otherwise specified.

EXAMPLES

EXAMPLES 1 to 17

General procedure

In a reactor suitable for reactions with alkylene oxides, the cyclic dicarboxylic acid anhydride (liquid or solid) was introduced with stirring under nitrogen into the polyhydric alcohol and/or the dialkanolamine or a mixture of polyhydric alcohols and, in general, the catalyst either at room temperature or, if the alcohols were not liquid, at elevated temperature, followed by rapid heating to 90°–130° C. (depending upon the viscosity of the semiester formed). The mixture was then left to react for 2 hours at that temperature. Thereafter, unless the catalyst was added in the first stage, the alkylene oxide was introduced after its addition at 90° to 130° C. under a nitrogen pressure of 1 to 3 bar, followed by an afterreaction for at least 5 h at 100° to 130° C. Any traces of free alkylene oxide were then removed by distillation under reduced pressure. 14 formulations using the resulting oligoesters according to the invention and 3 Comparison Examples using catalysts known from the literature are compared in Table 1 below, in which the abbreviations used have the following meanings:

| | |
|---|---|
| PAA = phthalic acid anhydride | EG = ethylene glycol |
| MAA = maleic acid anhydride | DEG = diethylene glycol |
| SAA = succinic acid anhydride | PG = propylene glycol |
| EO = ethylene oxide | Gly = glycerol |
| PO = propylene oxide | |

Catalyst A: reaction product of ethylenediamine with 5 moles of PO
Catalyst B: reaction product of propylenediamine with 7 moles of PO
Catalyst C: triisopropanolamine

TABLE 1

| Example No. | Carboxylic acid anhydride | Polyhydric alcohol | Molar ratio COOH:OH | Catalyst* % by weight | | Alkylene oxide molar ratio COOH:alkylene oxide | OH number | Acid number | Viscosity 25° (mPas) |
|---|---|---|---|---|---|---|---|---|---|
| 1 | PAA | DEG | 1:0.6 | 1 | A | EO 1:1.2 | 252 | 1.5 | 20900 |
| 2 | PAA | DEG | 1:0.8 | 1 | A | EO 1:1.3 | 310 | 0.8 | 5900 |
| 3 | PAA | DEG | 1:0.8 | 1 | A | PO 1:1.3 | 287 | 3.7 | 8860 |
| 4 | PAA | DEG | 1:1.5 | 1 | A | EO 1:1.5 | 430 | 0.1 | 780 |
| 5 | PAA | EG | 1:0.7 | 0.5 | C | EO 1:1.0 | 320 | 4.1 | 20100 |
| 6 | PAA | EG | 1:0.8 | 1 | C | EO 1:1.3 | 350 | 3.1 | 9800 |
| 7 | PAA | EG | 1:1.0 | 0.5 | C | EO 1:1.4 | 410 | 1.2 | 5300 |
| 8 | PAA | Gly | 1:1.0 | 1 | B | EO 1:1.7 | 520 | 0.3 | 45800 |
| 9 | PAA | DEG/sorbitol 0.75/0.25 | 1:1.0 | 1 | B | PO 1:1.6 | 460 | 2.5 | 41900 |
| 10 | PAA | DEG/sorbitol 0.6/0.2 | 1:0.8 | 1 | B | EO 1:1.5 | 425 | 3.3 | 54500 |
| 11 | MAA | DEG | 1:0.6 | 0.5 | A | EO 1:1.3 | 298 | 1.5 | 2460 |
| 12 | PAA | diethanolamine | 1:1 | 0.5 | C | EO 1:1.2 | 306 | 9.4 | 85300 |
| 13 | SAA | DEG/diethanolamine 0.5/0.5 | 1:1 | 0.5 | A | EO 1:1.2 | 302 | 4.1 | 20340 |
| 14 | SAA | PG | 1:0.8 | 1 | B | PO 1:1.3 | 375 | 3.2 | 4250 |
| 15 (Comp.) | PAA | DEG | 1:0.8 | 1 | KCl | EO 1:1.3 | 308 | 2.6 | 8810 |
| 16 (Comp.) | PAA | DEG | 1:0.8 | 0.2 | methyl-imidazole | EO 1:1.3 | 307 | 0.2 | 8930 |
| 17 (Comp.) | PAA | DEG/sorbitol 0.75/0.25 | 1:1.0 | 1 | LiCl | PO 1:1.6 | 461 | 0.8 | 84130 |

*based on end product

Figure 2:
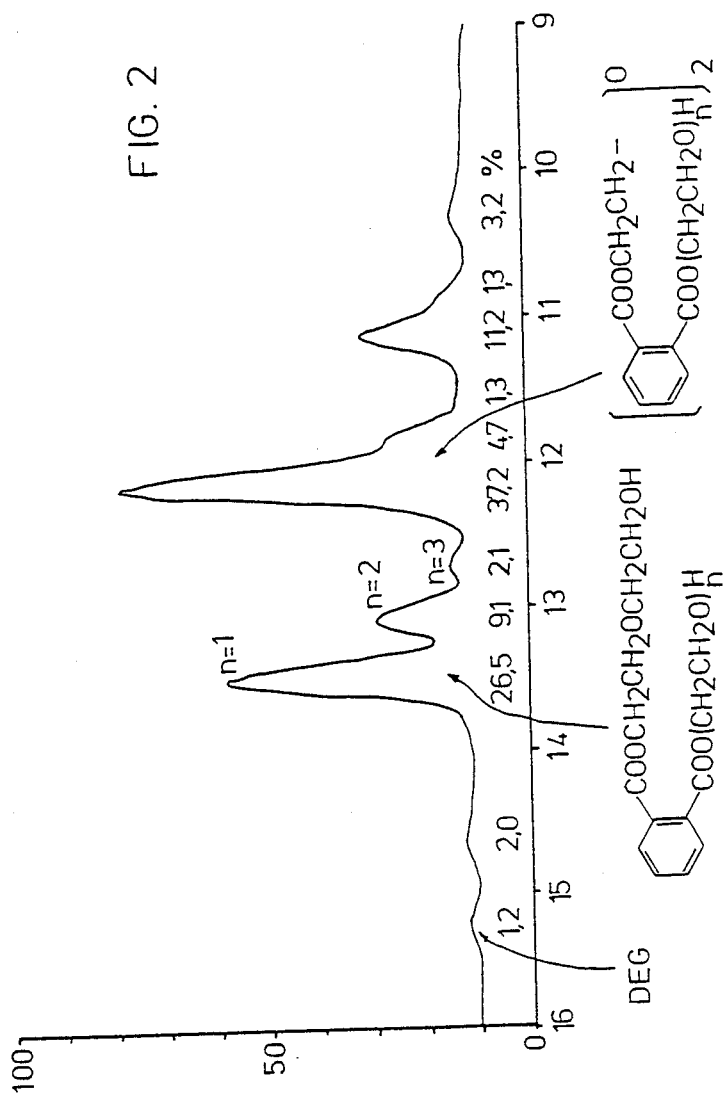
Figure 3:
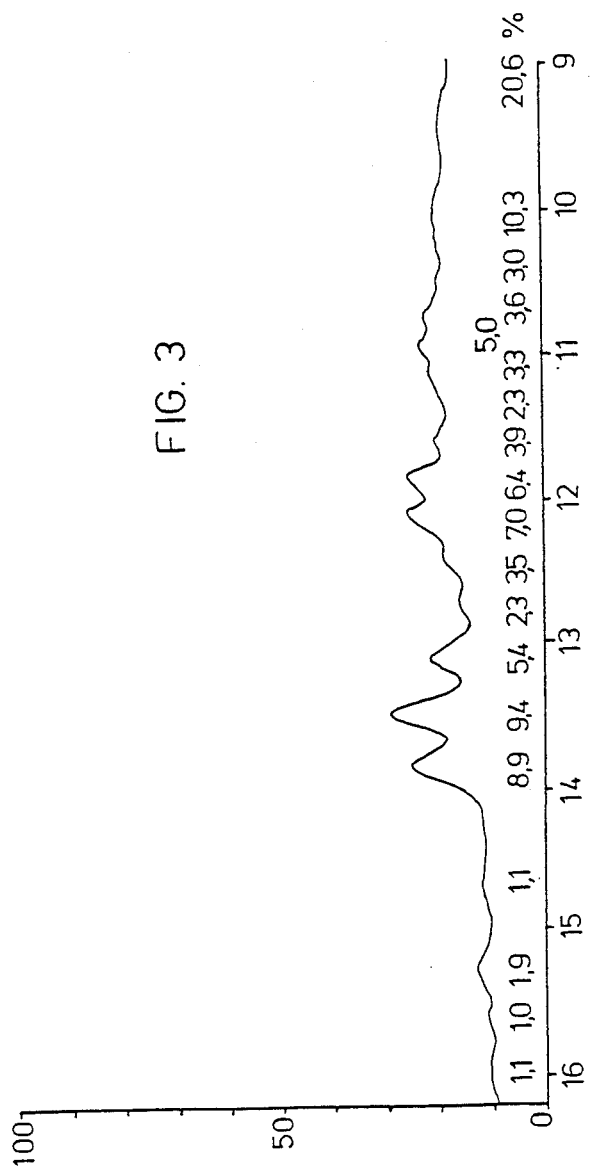
FIG. 3 is a gel chromatogram of the product of comparative Example 15.
Figure 4:
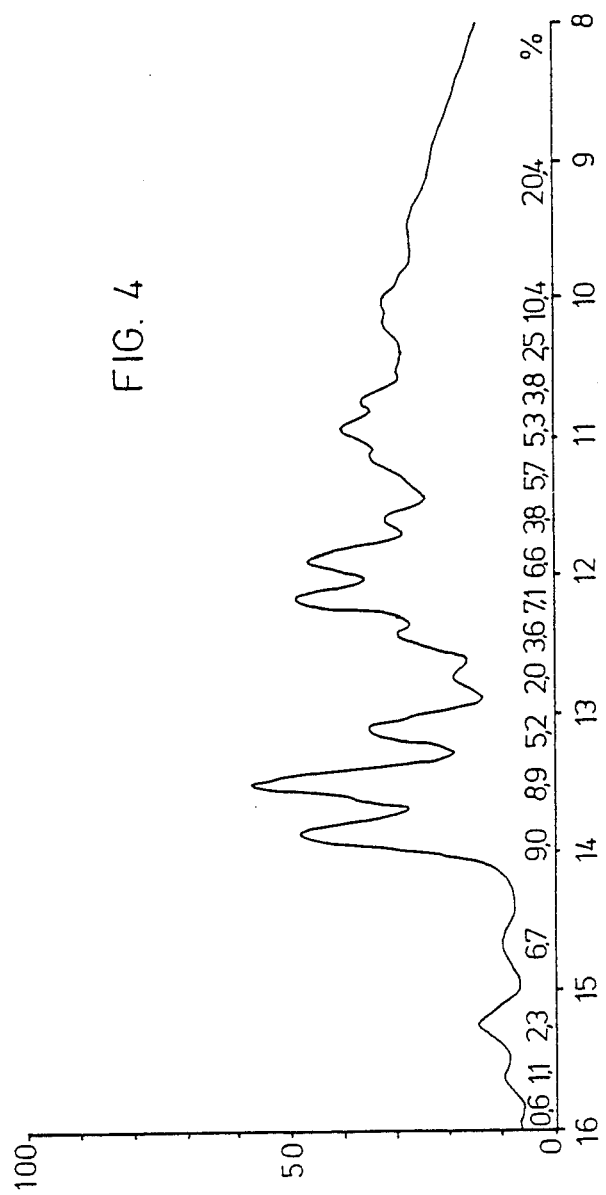
FIG. 4 is a gel chromatogram of the product of comparative Example 16.

The gel chromatograms in FIGS. 1–4 for Example 2 (FIGS. 1 and 2) and Comparison Examples 15 (FIG. 3) and 16 (FIG. 4) demonstrate the exceptional position of the catalysts according to the invention.

Apart from diethylene glycol (DEG), gel chromatogram 1 of the semiester corresponding to Example 2 (FIG. 1) essentially shows only the reaction products of 1 mole phthalic acid anhydride and 1 mole diethylene glycol and the reaction product of 2 moles phthalic acid anhydride and 1 mole diethylene glycol.

Gel chromatogram 2 of the oligoester corresponding to Example 2 (FIG. 2) essentially shows the original narrow molecular weight distribution.

Gel chromatograms 3 and 4 of Comparison Examples 15 and 16 (FIGS. 3 and 4 respectively) show that use of known catalysts rather than the inventive catalyst in a formulation which is otherwise the same as that of Example 2 results in a product with a molecular weight distribution which is considerably broadened by transesterification, esterification and etherification, leading to the increased viscosity determined.

APPLICATION EXAMPLES 18–26

In Tables 2 and 3 exemplary formulations for materials produced in accordance with the present invention are given. Table 2 lists formulations for rigid polyurethane or polyurethane urea foams and the properties of these foams, Table 3 lists formulations for rigid foams containing polyisocyanurate structures in which the oligoesters of the present invention were employed and the properties of those foams.

The oligoesters and polyethers listed in the Tables were manually foamed. The starting materials were first thoroughly intermixed and, after addition of the indicated quantity of isocyanate, were stirred for 10 to 15 seconds and the poured into an open mold.

Free foams measuring 30 cm×30 cm×30 cm were formed. The hardening of these foams was determined by a manual method so that the results can only be evaluated relative to one another. Burning behavior was tested in accordance with DIN 4102.

Starting materials:

The isocyanates used were commercial polyphenyl-polymethylene polyisocyanates obtained by phosgenation of aniline-formaldehyde condensates and having NCO-contents of 31% by weight (Desmodur 44V20 and Desmodur 44V70, products of Bayer AG).

The oligoesters of the present invention produced in Examples 2, 3 and 9 were used.

Comparison polyethers:

Commercial polyether polyols based on sucrosepropylene glycol-ethylene glycol-propylene oxide having OH numbers of 460 (Desmiphen® VP PU 1240=polyether polyol 1) and 470 (Desmophen® 4034 B=polyether polyol 2), products of Bayer AG, Leverkusen.

Flameproofing agent:

Diphenyl cresyl phosphate: Disflamoll® DPK, a product of Bayer AG.

Activators:

Dimethylcyclohexylamine: Desmorapid® 726 b a product of Rhein-Chemie, Rheinau. PIR activator: trimerization catalyst based on potassium acetate.

(R 11=trifluoromethane)

TABLE 2

| | Ex. 18 | Ex. 19 | Ex. 20 |
|---|---|---|---|
| Polyether polyol 1 (pbw) | 20 | 20 | 20 |
| Example 2 Oligoester (pbw) | 80 | | |
| Example 3 Oligoester (pbw) | | 80 | |
| Example 9 Oligoester (pbw) | | | 80 |
| Water (pbw) | 2.1 | 2.1 | 2.1 |
| Stabilizer | | | |
| VP AC 3378 (pbw) | 1.8 | 1.8 | 1.8 |
| Desmorapid ® 726 b (pbw) | 1 | 1 | 1 |
| R 11 (pbw) | 43 | 43 | 43 |
| Desmodur ® 44V20 | 123 | 123 | 152 |
| Cream time (s) | 26 | 23 | 27 |
| Gel time (s) | 84 | 85 | 85 |
| Hardening (mins.) | 10.5 | 10.5 | 8 |
| Gross density (kg/m³) | 20 | 20 | 21 |

TABLE 3

|  | Ex. 21 | Ex. 22 | Ex. 23 | Ex. 24 | Ex. 25 | Ex. 26 |
| --- | --- | --- | --- | --- | --- | --- |
| Polyether polyol 2 (pbw) | 60 | 60 | 60 | 60 | 60 | 60 |
| Example 2 Oligoester (pbw) | 20 | 40 |  |  |  |  |
| Example 3 Oligoester (pbw) |  |  | 20 | 40 |  |  |
| Example 9 Oligoester (pbw) |  |  |  |  | 20 | 40 |
| Disflamoll DPK (pbw) | 20 | 20 | 20 | 20 | 20 | 20 |
| Stabilizer |  |  |  |  |  |  |
| VP AC 3278 (pbw) | 1 | 1 | 1 | 1 | 1 | 1 |
| Desmorapid 726 b (pbw) | 1 | 1 | 1.2 | 1 | 1.7 | 1.7 |
| PIR-activator (pbw) | 2.5 | 2.5 | 2.7 | 2.5 | 3.7 | 3.7 |
| R 11 (pbw) | 40 | 40 | 40 | 40 | 40 | 40 |
| Desmodur 44V70 (pbw) | 300 | 300 | 300 | 300 | 300 | 300 |
| Index | 368 | 314 | 368 | 314 | 338 | 270 |
| Cream time (s) | 33 | 30 | 34 | 34 | 35 | 32 |
| Gel time (s) | 89 | 71 | 98 | 102 | 103 | 90 |
| Gross density (kg/m$^3$) | 50 | 51 | 50 | 51 | 51 | 50 |
| Flammability classification according to DIN 4102 | B2 | B2 | B2 | B2 | B2 | B2 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a hydroxyl group containing oligoesters having an OH number of from 200 to 600 mg KOH/g in which no halogen is present comprising (a) reacting
   (1) a non-halogenated cyclic dicarboxylic acid anhydride
   with
   (2) polyfunctional alcohols and/or dialkanolamines in a molar ratio of 1:0.5 to 1:1.5 at a temperature of from 50° to 150° C. to form the corresponding dicarboxlic acid semiester and/or semiamide and (b) alkoxylating the carboxyl groups present in the reaction product of (a) with ethylene oxide and/or propylene oxide at a temperature of from 80° to 150° C. and in quantities such that the equivalent ratio of acid groups to alkylene oxide groups is from 1:0.08 to 1:1.7 in the presence of a reaction product of alkoxides with at least 3 C-atoms with ammonia, piperidine, piperazine and/or $C_2$-$C_6$ aliphatic, polyamines, preferably diamines in which all of the NH-functional groups have been alkoxylated.

2. The process of claim 1 in which (a) is carried out at a temperature of from 90° to 130° C.

3. The process of claim 1 in which the molar ratio of cyclic dicarboxylic acid anhydride to polyfunctional alcohol and/or dialkanolamine is from 1:0.7 to 1:1.2.

4. The process of claim 1 in which the propoxylation product present in (b) is a propoxylation product of ammonia, ethylene diamine, propylene diamine or hexamethylenediamine.

5. The process of claim 4 in which from 0.5 to 5 parts by weight propoxylation product are present for every 100 parts by weight oligoester.

6. The process of claim 1 in which the cyclic dicarboxylic acid anhydrides is selected from phthalic acid anhydride, maleic acid anhydride, glutaric acid anhydride and mixtures thereof.

7. The process of claim 1 in which (a)(2) is a polyfunctional alcohol.

8. The process of claim 7 in which the polyfunctional alcohol is a diol having a molecular weight of from 62 to 182.

9. The process of claim 7 in which the polyfunctional alcohol is selected from trihydric alcohols, tetrahydric alcohols, pentahydric alcohols, hexahydric alcohols and mixtures thereof having a molecular weight of from 62 to 182.

10. The process of claim 7 in which the polyfunctional alcohol is a mixture of a diol with a trihydric to hexahydric polyol having a molecular weight of from 62 to 182.

11. A process for the production of a polyisocyanate addition product comprising reacting the oligester produced in claim 1 with an organic polyisocyanate.

12. The process of claim 11 in which the reaction is carried out in the presence of a blowing agent and/or a chain extending agent and/or a crosslinking agent and-/or a catalyst.

13. A polyurethane foam produced by the process of claim 12.

14. A polyisocyanate addition product produced by the process of claim 11.

* * * * *